United States Patent [19]

Ali et al.

[11] Patent Number: 6,071,904
[45] Date of Patent: Jun. 6, 2000

[54] PROCESS FOR MANUFACTURING OPHTHALMIC SUSPENSIONS

[75] Inventors: Yusuf Ali; Robert E. Beck, both of Fort Worth; Rex C. Sport, Grapevine, all of Tex.

[73] Assignee: Alcon Laboratories, Inc., Fort Worth, Tex.

[21] Appl. No.: 08/886,933

[22] Filed: Jul. 2, 1997

Related U.S. Application Data

[60] Provisional application No. 60/032,820, Dec. 11, 1996.
[51] Int. Cl.$^7$ .................................................. A61K 31/54
[52] U.S. Cl. ........................................ 514/222.8; 514/912
[58] Field of Search ................................. 514/222.8, 912

[56] References Cited

U.S. PATENT DOCUMENTS 5,362,758  11/1994  Ahmed ..................................... 514/777
5,378,703  1/1995  Dean et al. ........................... 514/222.8

FOREIGN PATENT DOCUMENTS

| | | |
|---|---|---|
| 0601619A2 | 5/1993 | European Pat. Off. . |
| 0602702A1 | 6/1994 | European Pat. Off. . |
| 0509752A2 | 7/1994 | European Pat. Off. . |
| WO 93/16701 | 8/1993 | WIPO . |

OTHER PUBLICATIONS

Martin, F. et al. "Sterilisation par la Chaleur des Solutions de Sulfamides", Journal de Pharmacie de Belgique, vol. 25, No. 4, pp. 317–329, Jul.–Aug. 1970.

*Primary Examiner*—Zohreh Fay
*Attorney, Agent, or Firm*—Sally Yeager

[57] ABSTRACT

Ophthalmic suspensions containing brinzolamide or brinzolamide and a beta-blocker and processes for manufacturing the suspensions are disclosed.

12 Claims, 3 Drawing Sheets

PROCESS FOR MANUFACTURING OPHTHALMIC SUSPENSIONS

Priority is claimed from the provisional application, U.S. patent application Ser. No. 60/032820, filed Dec. 11, 1996.

This invention relates to sterile topical ophthalmic suspensions containing a carbonic anhydrase inhibitor or a carbonic anhydrase inhibitor and a beta-blocker and processes for making the suspensions. The suspensions are useful in controlling the elevated intraocular pressure in persons suffering from ocular hypertension or primary open angle glaucoma.

BACKGROUND OF THE INVENTION

Sterile, topical, ophthalmic suspensions have typically been manufactured in the past in one of three ways: by bulk sterilization of a milled suspension, by aseptic addition of sterile micronized raw material into a sterile vehicle, or by aseptic addition of a sterile raw material to a sterile menstruum followed by ball milling and aseptic addition of the sterile concentrate into a sterile vehicle.

The present suspensions, containing a carbonic anhydrase inhibitor (CAI) or a CAI and a beta-blocker, can not be made via these routes. Due to the solubility of the CAI at autoclaving temperatures, large needle-like crystals form on cool down of the final formulation. Aseptic ball milling of this final formulation is not practical. Aseptic addition of the CAI to a sterile vehicle is also not practical as the CAI cannot be sterilized by conventional means. Dry heat sterilization causes melting of the material. Sterilization of the CAI by ethylene oxide introduces unacceptable degradation products and residues, and sterilization by gamma irradiation of micronized material produces degradation products unacceptable for regulatory filing.

The present process provides a procedure for making a CAI or a CAI/beta-blocker suspension on a manufacturing scale without the problems described above.

SUMMARY OF THE INVENTION

The present invention is directed to a CAI and a CAI/beta-blocker suspension, processes for making them, and a "bottle" for use in the processes.

DETAILED DESCRIPTION OF PREFERRED EMBODIMENTS

The present CAI suspension contains the pharmaceutically active CAI, R 4-ethylamino-3,4-dihydro-2-(3-methoxy)propyl-2H-thieno [3,2-e]-1,2-thiazine-6-sulfonamide 1,1 dioxide, which is known as brinzolamide. This compound is disclosed in commonly assigned U.S. Pat. No. 5,378,703 (Dean, et al.). The present suspension and the process for making it are not disclosed in Dean, et al.

Figure 1:
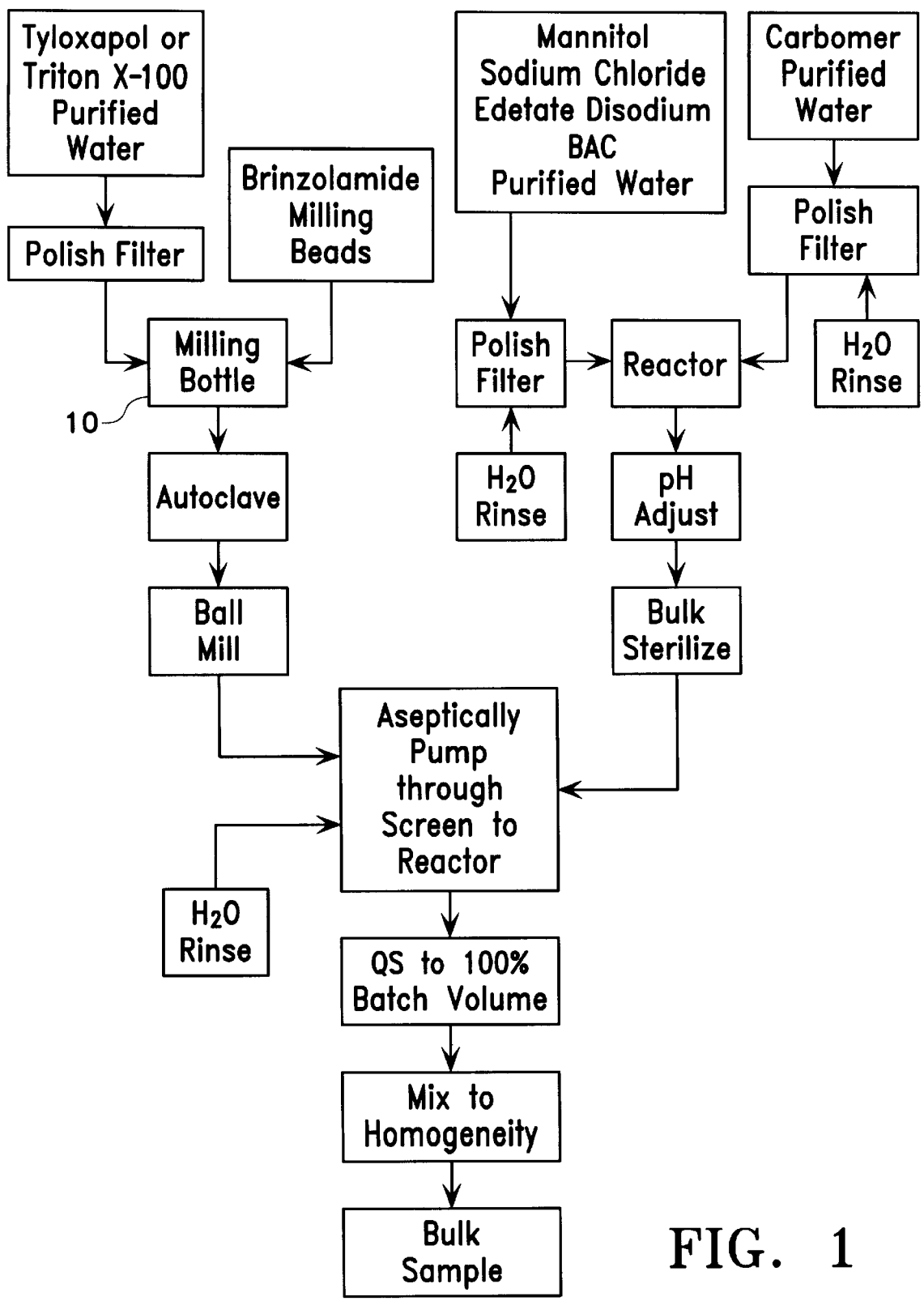
FIG. 1 is a flow diagram showing the process for making brinzolamide ophthalmic suspension.

The process for making the brinzolamide suspension uses autoclaving of a concentrated slurry of brinzolamide in milling bottle 10, ball milling of the hot slurry, and then adding the slurry to the rest of the ingredients as shown in FIG. 1.

Referring now to FIG. 1, first the milling menstruum containing either Tyloxapol, (4-(1,1,3,3-tetramethylbutyl) phenol polymer with formaldehyde and oxirane), available from Sterling Co. or Triton X-100, ($\alpha$-[4-(1,1,3,3-tetramethylbutyl)phenyl]-$\omega$-hydroxypolyoxy-1,2-ethane diyl), available from Rohm and Haas Corp. is prepared. The milling menstruum is critical to the manufacture of this suspension. Use of menstrua containing surfactants other than Tyloxapol or Triton X-100, such as Polysorbate 80, (sorbitan mono-9-octadecenoate poly (oxy-1,2-ethanediyl) derivatives), a common wetting agent for use in ophthalmic suspensions, results in inadequate milling of large crystals of brinzolamide which form during cool down following autoclaving. Use of Tyloxapol or Triton X-100 at concentrations of about 0.001 to 5 weight percent (wt. %) in the milling menstruum unexpectedly minimizes foaming and allows for adequate milling of the crystals. Although use of either Tyloxapol or Triton X-100 in the milling menstruum is acceptable, Tyloxapol at concentrations of 0.01 to 0.10 wt. % in the final suspension is the preferred agent as Triton X-100 is not commonly used in ophthalmic preparations.

Once the milling vehicle is prepared it is filtered and then mixed with milling beads, such as, alumina, glass, or zirconia, preferably 3mm zirconia-Y beads and added to milling bottle 10. The mixture is then autoclaved in milling bottle 10 at normal temperatures and pressures known to those skilled in the art, e.g., 121–129° C., preferably 123–127° C., for 30–45 minutes. After autoclaving and while the slurry is above 80° C., the mixture is ball milled under conditions to achieve an average particle size of 0.2–10 $\mu$m, preferably 1–5 $\mu$m, preferably 18–19 hours at 50–55 RPM.

After milling, the milled slurry is aseptically added through a screen with smaller openings than the milling bead size to the rest of the ingredients including, water, one or more tonicity agents, such as, but not limited to, mannitol or sodium chloride; one or more preservatives, including, but not limited to, benzalkonium chloride or one of its derivatives, polyquaternium 1, thimerosol or EDTA; and at least one polymer, including, but not limited to carbomer, hydroxypropylmethylcellulose (HPMC), hydroxyethylcellulose (HEC), or polyvinylalcohol (PVA) which are mixed, filtered, pH adjusted, and sterilized prior to their combination with the milled mixture. Preferable ingredients are mannitol, NaCl, EDTA, BAC, carbomer, such as Carbopol 934P or 974P.

Sterile, purified water used to rinse the beads is then added to the mixture and the batch is brought to final volume. The ingredients are mixed until homogeneous.

The CAI/beta-blocker suspension contains brinzolamide, but also includes a beta-blocker, such as, (S)-1-[(1,1-dimethylethyl)amino]-3-[[4-(4-morpholinyl)-1,2,5-thiadiazol-3-yl]oxy]-2-propanol (Z) 2-butenedioate (1:1) salt, which is known as timolol maleate or (±) 1-[p-[2-(cyclopropylmethoxy)ethyl]phenoxy]-3-(isopropylamino)-Z-propanol hydrochloride, which is known as betaxolol hydrochloride. Different isomers, for example, S-betaxolol, and salts can be used. A sterile ophthalmic solution containing timolol maleate (Timoptic®) is available from Merck and Co., Inc. It is useful for the treatment of elevated intraocular pressure in persons with ocular hypertension or open angle glaucoma. A sterile ophthalmic solution containing betaxolol hydrochloride (Betoptic®) is available from Alcon Laboratories, Inc. It is also useful for the treatment of ocular hypertension and open angle glaucoma.

Figure 2:
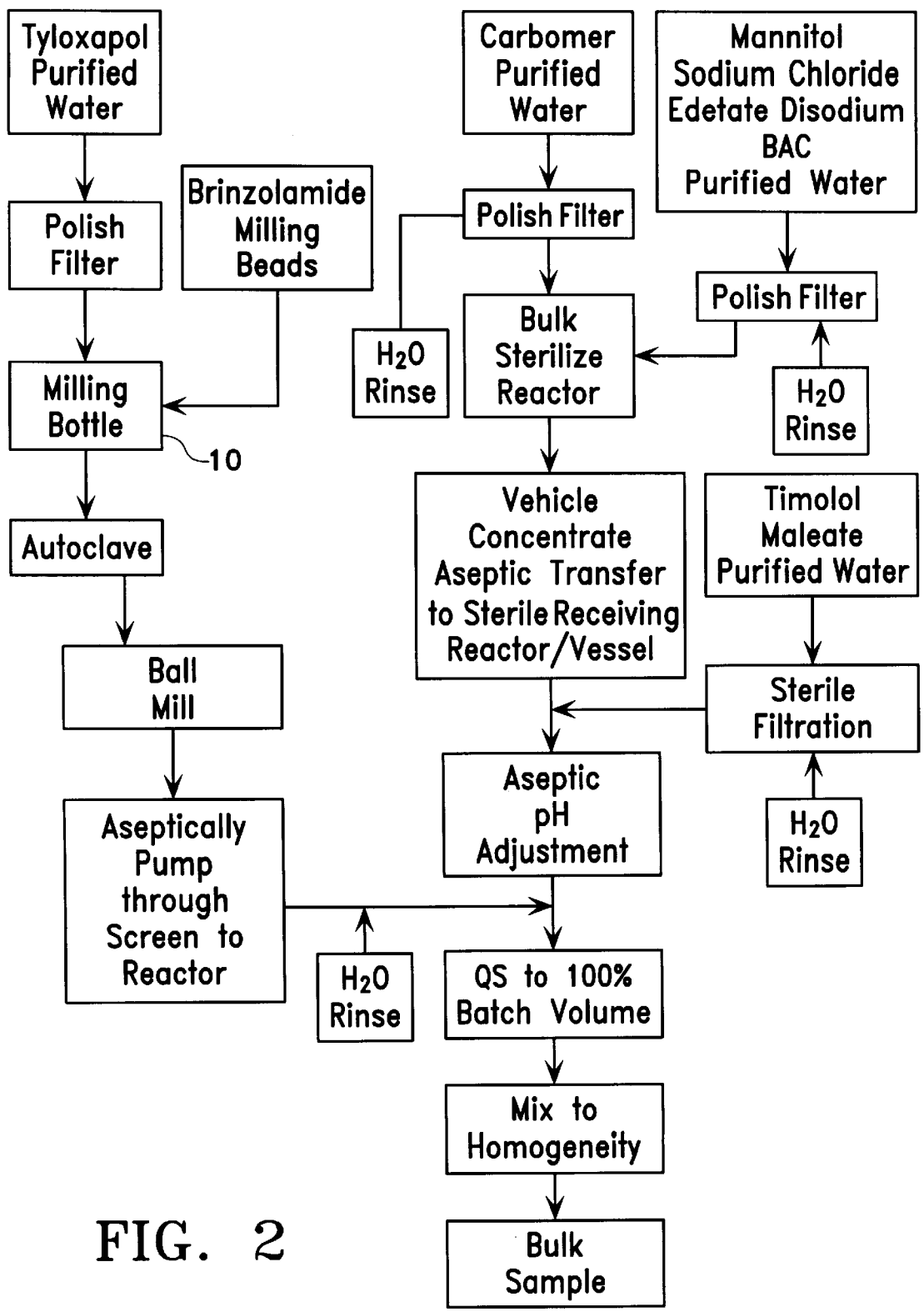
FIG. 2 is a flow diagram showing the process for making brinzolamide/timolol ophthalmic suspension.

The process for making the CAI/beta-blocker suspension is similar to that for making the brinzolamide suspension described above. The process for making a CAI/beta-blocker suspension in which the beta-blocker is sensitive to heat and must be aseptically filtered (e.g. timolol maleate) is shown in FIG. 2. If the beta-blocker to be used can be autoclaved (e.g. betaxolol), it can be added with the mannitol and other listed ingredients to make the vehicle concentrate.

Referring now to FIG. 2, the process for handling brinzolamide is the same as shown in FIG. 1. The process for making the combination differs in that timolol maleate is incorporated by sterile filtration into the sterilized vehicle concentrate which is then aseptically pH adjusted to 6.0–8.0, preferably 6.5–7.6, and most preferably 7.0–7.4. The concentrate is then combined with the brinzolamide composition and mixed until homogeneous.

Figure 3:
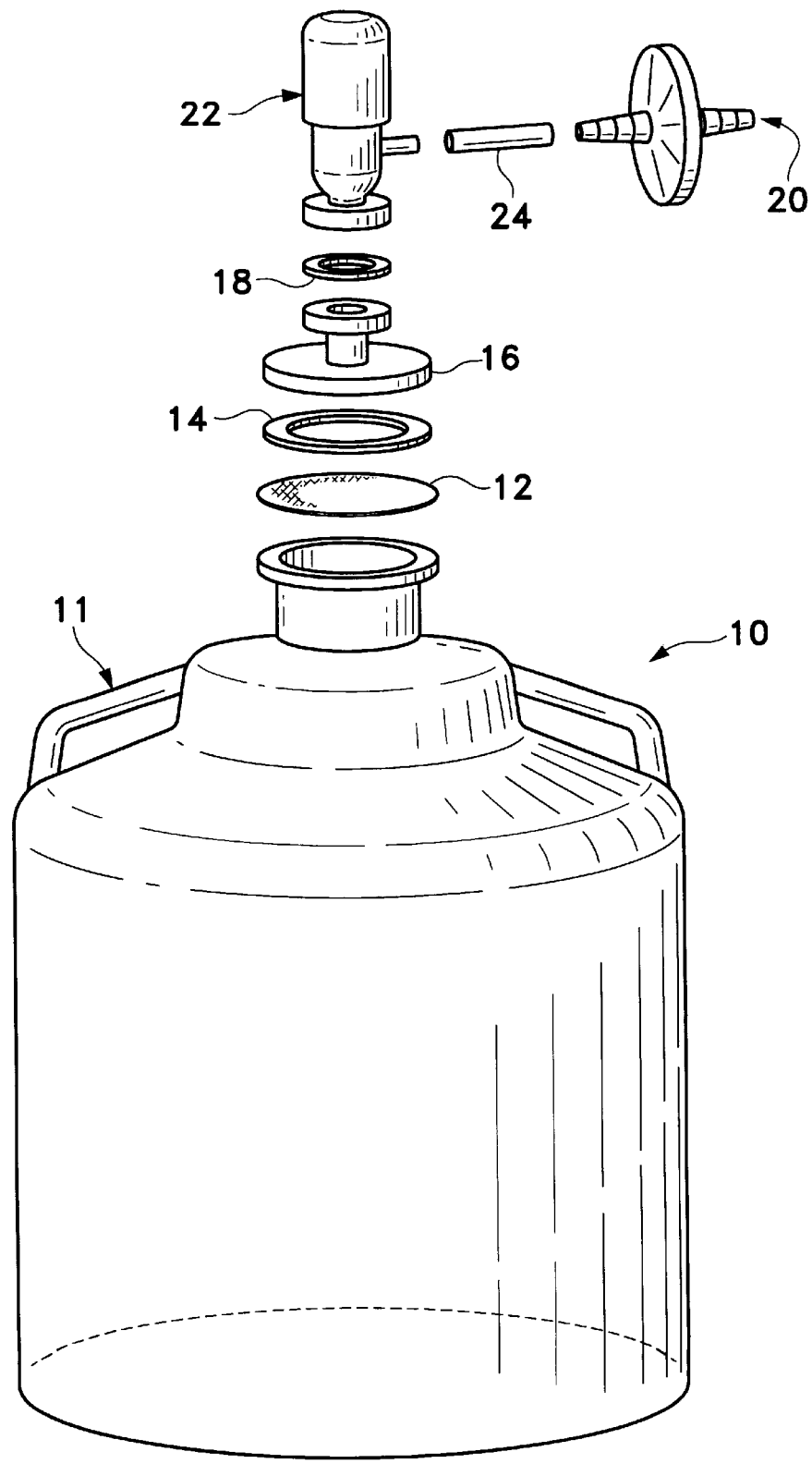
FIG. 3 is an expanded side view of one milling bottle that may be used in the present invention.

As shown in FIG. 3, milling bottle 10 includes carboy 11 and filter 12. Carboy 11 preferably is made from a material that can withstand autoclaving, such as polypropylene, and is sufficiently large so as to contain the suspension and the milling slurry, for example, ten liters. Filter 12 preferably is a hydrophobic filter having a pore size of 0.2 to 10 μm, preferably 1–5 μm, and made from any hydrophobic material of sufficient mechanical strength which is steam sterilizable. One filter 12 suitable for use in the present invention is commercially available from Millipore under the tradename DURAPEL 2 μm. Filter 12 prevents the suspension and the milling slurry from expanding out of carboy 11 during autoclaving, but allows for pressure equalization during heating and cooling.

Excess pressure in carboy 11 is vented through bleed valve 22 and air is allowed to enter aseptically carboy 11 through vent filter 20 which is connected to bleed valve 22 by tubing 24. Vent filter 20 preferably is a hydrophobic filter having a pore size of 0.2 μm. Bleed valve 22 is connected to carboy 11 by connector 16 and the entire assembly is sealed by gaskets 14 and 18.

The formulations of the present invention are set forth in the following examples.

EXAMPLE 1

| Ingredient | Concentration (wt. %) |
| --- | --- |
| Brinzolamide | 1.0% plus 5% excess |
| Tyloxapol | 0.025 |
| Carbomer 974P | 0.40 |
| Edetate Disodium | 0.01 |
| BAC | 0.01 plus 5% excess |
| Mannitol | 3.30 |
| Sodium Chloride | 0.25 |
| Purified Water | q.s. 100% |

EXAMPLE 2

| Ingredient | Concentration (wt. %) |
| --- | --- |
| Brinzolamide | 1.0% plus 5% excess |
| Triton X-100 | 0.025 |
| Carbomer 974P | 0.40 |
| Edetate Disodium | 0.01 |
| BAC | 0.01 plus 5% excess |
| Mannitol | 3.30 |
| Sodium Chloride | 0.25 |
| Purified Water | q.s. 100% |

EXAMPLE 3

The formulation in Example 1 was made as follows:

A. Preparation of Milling Slurry

1. Into a suitable compounding vessel containing a stir-bar approximately 2300 g of hot (50–70° C.) purified water were added. 15.0 g of tyloxapol were added to the vessel and the ingredients were mixed until homogeneous.

2. The tyloxapol solution was brought to 2700 g using hot (50–70° C.) purified water.

3. The tyloxapol solution was filtered through a 10 μm polishing filter and held for use in the milling slurry.

4. The following materials were combined in carboy 11:

| | |
| --- | --- |
| 3 mm Zirconia-Yttria beads | 22 kg |
| Tyloxapol milling solution (Step 3) | 2700 g |
| Brinzolamide | 640 g |

5. Filter 12, gaskets 14 and 18, connector 16, bleed valve 22, vent filter 20 and tubing 24 were placed securely on carboy 11.

6. Milling bottle 10 and its ingredients were autoclaved on standard fast cool cycle.

7. Milling bottle 10 was removed immediately after completion of the autoclave cycle was ball milled at 50–55 RPM for 18–19 hours.

8. The milling slurry was then held for use in aseptic addition.

B. Preparation of Carbomer Slurry 1. 84 kg of hot (50–70° C.) purified water were transferred to a suitable compounding vessel with an agitator.

2. 1380 g of Carbomer 974P were added to the water and dispersed with high speed agitation until homogeneous.

3. The Carbomer slurry was brought to 86.25 kg with purified water and mixed to homogeneity.

C. Preparation of Vehicle Concentrate

1. Approximately 100 kg of hot (50–70° C.) purified water were added to a suitable compounding vessel with an agitator.

2. The following ingredients were added in the order listed using moderate agitation:

| | |
| --- | --- |
| Mannitol | 10.56 kg |
| Sodium Chloride | 800 g |
| Edetate Disodium | 32 g |
| Benzalkonium Chloride, 10% Solution | 336 g |

3. The solution was filtered through a polishing filter and added to a 300 L reactor. The compounding vessel and filter were rinsed with approximately 15 L of hot (50–70° C.) purified water which was added to the reactor.

4. 80 kg of Carbomer 974P slurry (Section B) was added to the solution with mixing.

5. The mixture of 4 was agitated and the pH adjusted to 7.5±0.2 using 1N sodium hydroxide (and 1N hydrochloric acid if necessary). Approximately 16 L of 1N NaOH were required.

6. The vehicle concentrate was adjusted to 230.4 kg and sterilized using steam at 121–128° C. for 35 minutes.

7. The vehicle concentrate was cooled to approximately room temperature (less than 30° C.) and held for use in aseptic processing.

8. 43 kg of the vehicle concentrate was aseptically transferred to a sterile mixing tank in a clean room.

E. Aseptic Addition of Milling Slurry 1. 15 kg of purified water were sterilized in glass carboys in an autoclave.

2. A transfer set up including stainless steel tubing, silicone tubing, and stainless steel screens was autoclaved and transferred to the clean room.

3. The milling slurry was transferred through the screens and tubing into the vehicle concentrate.

4. The beads, tubing, screens, and carboy 11 were rinsed with purified water as necessary to transfer the milling slurry as completely as possible.

5. Sterile purified water was used to bring the batch weight to 61 kg. The batch was mixed until homogeneous.

EXAMPLE 4

| Ingredient | Concentration (wt. %) |
| --- | --- |
| Brinzolamide, NOC | 1.0% plus 5% excess |
| Timolol Maleate | 0.68* |
| Carbomer 974P | 0.4 |
| Sodium Chloride | 0.10 |
| Mannitol | 3.3 |
| Tyloxapol | 0.025 |
| Disodium Edetate | 0.01 |
| Benzalkonium Chloride | 0.01 plus 5% excess |
| Sodium Hydroxide or Hydrochloric Acid | Adjust pH 7.2 ± 0.2 |
| Purified Water | q.s. 100% |

*Equivalent to 0.5% Timolol as free base

EXAMPLE 5

The formulation in Example 4 was made as follows:

A. Preparation of Milling Slurry

1. Into a suitable compounding vessel containing a stir-bar approximately 200 g of hot (50–70° C.) purified water were added. 1.25 g of tyloxapol were added to the vessel and the ingredients were mixed until homogeneous.

2. The tyloxapol solution was brought to 300 g using hot (50–70° C.) purified water.

3. The tyloxapol solution was filtered through a polishing filter and held for use in the milling slurry.

4. The following materials were combined in a milling bottle:

| 3 mm Zirconia-Yttria beads | 2180 g |
| --- | --- |
| Tyloxapol milling solution (Step 3) | 300 g |
| Brinzolamide | 52.6 g |

5. The milling bottle and its ingredients were autoclaved on standard fast cool cycle.

6. The milling bottle was removed immediately after completion of the autoclave cycle and ball milling was begun at 50–55 RPM for 18–19 hours.

7. The milling slurry was then held for use in aseptic addition.

B. Preparation of 2% Carbomer Slurry 1. 4000 g of hot (50–70° C.) purified water were transferred to a suitable compounding vessel with an overhead mixer.

2. 80.0 g of Carbomer 974P were added to the water and dispersed with high speed agitation until homogeneous.

3. The Carbomer slurry was brought to 5000 g with purified water and mixed to homogeneity.

4. 1250 g of the slurry were added to a vessel through a polish filter (40 $\mu$m) and covered.

C. Preparation of Vehicle Concentrate

1. Approximately 1000 g of hot (50–70° C.) purified water were added to a suitable compounding vessel with an agitator.

2. The following ingredients were added in the order listed using moderate agitation:

| Mannitol | 165 g |
| --- | --- |
| Sodium Chloride | 5.00 g |
| Edetate Disodium | 0.500 g |
| Benzalkonium Chloride, 10% Solution | 5.25 g |

3. The dispersion was filtered through a polishing filter and added to a 5 L glass screw cap media bottle. The compounding vessel and filter were rinsed with approximately 300 mL of hot (50–70° C.) purified water and added to the glass media bottle.

4. The Carbomer 974P slurry (Section B) was added to the dispersion with mixing. Its vessel was rinsed with 250 mL of purified water which was added to the glass media bottle.

5. The vehicle concentrate was brought to 2750 g with purified water.

6. 200 mL of 6N NaOH were prepared in a beaker.

7. 51.0 g of timolol maleate were dissolved in 1074 g purified water.

D. Preparation for Aseptic Addition

1. Approximately 1000 mL of purified water were added to each of two 2 L glass screw cap media bottles with 0.2 $\mu$m breather filters.

2. The following materials were autoclaved:
Miscellaneous glassware and utensils
Vehicle concentrate which includes the Carbomer slurry (Section C)
Purified water (Step 1)
Stainless steel tube with screen and silicone tubing
13 L carboy with stir bar
500 mL media bottle containing 1N HCl
500 mL media bottle with 0.2 $\mu$m filter for 6N NaOH 3. The vehicle concentrate was cooled to approximately room temperature (less than 30° C.) and held for use in aseptic processing.

E. Aseptic Compounding

1. All materials necessary for aseptic compounding, including milling slurry (Section A), vehicle concentrate (Section C), water, magnetic mixer, balance, tube, and screen, were taken to the clean room.

2. The 6N NaOH was sterile filtered into a sterile beaker.

3. The timolol maleate solution was sterile filtered into a sterile bottle and 750 g added to the vehicle concentrate.

4. The pH was aseptically adjusted to 7.2±0.2 with 6N NaOH. Approximately 52 g are required.

5. The milling slurry was transferred through the tube and screen into the vehicle concentrate.

6. The beads, tubing, and milling bottle were rinsed with purified water as necessary to transfer the milling slurry as completely as possible.

7. Purified water was used to bring the batch weight to (5094 g). The batch was mixed until homogeneous (not less than 15 minutes).

We claim:

1. A method for making a sterile ophthalmic suspension, which comprises;
   a. autoclaving a milling slurry comprising brinzolamide, milling beads, and a surfactant selected from the group consisting of tyloxapol and triton X-100;
   b. ball milling the milling slurry;
   c. preparing a polymer slurry comprising polymer and water;
   d. preparing a solution comprising tonicity and preservative agents;
   e. mixing the polymer slurry and the solution to form a vehicle concentrate and adjusting pH;
   f. autoclaving the mixture of step e; and
   g. aseptically adding the milling slurry through a screen to the mixture from step f.

2. The method of claim 1 wherein the surfactant is tyloxapol.

3. The method of claim 1 wherein the polymer slurry comprises carbomer.

4. The method of claim 1 wherein the solution of step d comprises mannitol, sodium chloride, edetate disodium, and benzalkonium chloride.

5. A method for making a sterile ophthalmic suspension, which comprises;
   a. autoclaving a milling slurry comprising brinzolamide, milling beads, and a surfactant selected from the group consisting of tyloxapol and triton X-100;
   b. ball milling the milling slurry;
   c. preparing a polymer slurry comprising polymer and water;
   d. preparing a solution comprising tonicity and preservative agents;
   e. mixing the polymer slurry and the solution to form a vehicle concentrate;
   f. autoclaving the mixture of step e;
   g. aseptically adding a timolol maleate solution to the mixture in step f;
   h. aseptically adjusting pH; and
   i. aseptically adding the milling slurry through a screen to the mixture of step g.

6. The method of claim 1 wherein the surfactant is tyloxapol.

7. The method of claim 1 wherein the polymer slurry comprises carbomer.

8. The method of claim 7 wherein the solution comprises mannitol, sodium chloride, edetate disodium, and benzalkonium chloride.

9. A method for making a sterile ophthalmic suspension, which comprises;
   a. autoclaving a milling slurry comprising brinzolamide, milling beads, and a surfactant selected from the group consisting of tyloxapol and triton X-100;
   b. ball milling the milling slurry;
   c. preparing a polymer slurry comprising polymer and water;
   d. preparing a solution comprising a beta-blocker and tonicity and preservative agents;
   e. mixing the polymer slurry and the solution to form a vehicle concentrate and adjusting pH;
   f. sterilizing the mixture of step e using steam; and
   g. aseptically adding the milling slurry through a screen to the mixture of step f.

10. The method of claim 9 wherein the surfactant is tyloxapol.

11. The method of claim 9 wherein the polymer slurry comprises carbomer.

12. The method of claim 9 wherein the solution comprises mannitol, sodium chloride, edetate disodium, and benzalkonium chloride.

* * * * *